United States Patent [19]

Tsutsumi et al.

[11] 4,097,403

[45] Jun. 27, 1978

[54] OIL-IN-WATER EMULSION AND EMULSIFYING OR SOLUBILIZING AGENT COMPOSITION USEFUL THEREIN

[75] Inventors: Hisao Tsutsumi, Sakura; Shizuo Hayashi, Sugitomachi; Hirokazu Nakayama; Toshinao Ukena, both of Wakayama, all of Japan

[73] Assignee: Kao Soap Co., Ltd., Tokyo, Japan

[21] Appl. No.: 760,962

[22] Filed: Jan. 21, 1977

[30] Foreign Application Priority Data

Feb. 5, 1976 Japan .................................. 51-11525

[51] Int. Cl.² ............................................. B01J 13/00
[52] U.S. Cl. ....................................... 252/312; 252/314; 252/356; 252/DIG. 1; 252/DIG. 7; 252/DIG. 14; 424/59; 424/70; 424/170
[58] Field of Search ................. 252/312, 356, DIG. 1; 424/170

[56] References Cited

U.S. PATENT DOCUMENTS

| 2,904,585 | 9/1959 | Doerr et al. ...................... 252/356 X |
| 3,954,658 | 5/1976 | Tsutsumi et al. ................ 252/356 X |

*Primary Examiner*—Richard D. Lovering
*Attorney, Agent, or Firm*—Blanchard, Flynn, Thiel, Boutell & Tanis

[57] ABSTRACT

An emulsifying or solubilizing agent composition comprising 58 to 95% by weight of a polyoxyethylene (10 to 100) sorbitol branched saturated fatty acid ($C_{11}$ to $C_{21}$) ester having from 3 to 6 ester groups in the molecule, 0.5 to 2.5% by weight of an alkali metal salt of a linear or branched fatty acid ($C_{11}$ to $C_{21}$), 2.5 to 6.0% by weight of a linear or branched fatty acid ($C_{11}$ to $C_{23}$) and 2 to 35% by weight of a branched saturated fatty acid ester of polyethylene glycol having an average molecular weight of from 150 to 2000.

10 Claims, No Drawings

OIL-IN-WATER EMULSION AND EMULSIFYING OR SOLUBILIZING AGENT COMPOSITION USEFUL THEREIN

BACKGROUND OF THE INVENTION

1. Field of the Invention

The present invention relates to an emulsifying or solubilizing composition which is capable of emulsifying or solubilizing liquid vegetable oils and highly polar synthetic ester oils which have heretofore been considered to be very difficult to emulsify or solubilize. The composition possesses excellent color and smell and excellent stability against photo-discoloration and decomposition.

2. Description of the Prior Art

As emulsifiers for cosmetics, there have heretofore been used non-ionic surface active agents such as polyoxyethylene sorbitan fatty acid esters, sorbitan fatty acid esters, glycerol fatty acid esters, polyethylene glycol fatty acid esters and polyoxyethylene alkyl ethers, and in addition, a great number of other non-ionic, anionic, cationic and amphoteric surface active agents. These emulsifiers, in general, have a good emulsifying power to mineral oils composed of hydrocarbons and the like and animal oils such as squalane and they provide stable emulsions of these oils. However, they scarcely emulsify liquid vegetable oils (hereinafter referred to as "vegetable oils") composed of triglycerides rich in alkyl groups having an unsaturated bond, such as camellia oil and olive oil, and esters (hereinafter referred to "synthetic esters") having at least one branched alkyl group, which are derived from branched or linear higher fatty acids and branched or linear higher alcohols, and stable emulsions of these oils cannot be obtained.

We previously discovered an emulsifying or solubilizing agent composition having a high emulsifying or solubilizing property to vegetable oils and synthetic ester oils. That composition was formed by mixing in specific weight ratios, an alkali metal salt of a fatty acid, a fatty acid and a polyethylene glycol unsaturated fatty acid ester-type surface active agent into a polyoxyethylene sorbitol unsaturated fatty acid ester-type surface active agent, (see the specification of Japanese patent application No. 91086/74, corresponding to U.S. Pat. No. 3,954,658).

That composition is satisfactory in its emulsifying and solubilizing properties, but it is defective in that it becomes colored or generates unwanted odors under some storage conditions and it is readily discolored when it is exposed to sun-light. This defect is serious when the composition is used for emulsifying cosmetics and the like.

SUMMARY OF THE INVENTION

We have discovered an improved emulsifying or solubilizing composition which possesses excellent emulsifying and solubilizing properties and which possesses, surprisingly, reduced tendency toward coloration and generation of bad odors.

More specifically, in accordance with the present invention, there is provided an emulsifying or solubilizing composition comprising I. from 58 to 95% by weight of a surface active agent of the polyoxyethylene sorbitol branched saturated fatty acid ester-type (hereinafter referred to as "component (I)") having the formula (A):

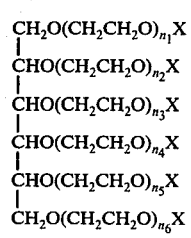

wherein the value of $n_1 + n_2 + n_3 + n_4 + n_5 + n_6$ is in the range of 10 to 100, and wherein from 3 to 6 of the total number of X's (i.e., 6) on the average of the mixture are branched saturated acyl (RCO-) groups having 11 to 21 carbon atoms (R is branched alkyl having 10 to 20 carbon atoms), the rest of the X's being hydrogen, II. from 0.5 to 2.5% by weight of an alkali metal salt of a linear or branched fatty acid having 11 to 21 carbon atoms (hereinafter referred to as "component (II)"), III. from 2.5 to 6.0% by weight of a linear or branched fatty acid having 11 to 23 carbon atoms (hereinafter referred to as "component (III)"), and IV. from 2 to 35% by weight of a branched saturated fatty acid ester of a polyethylene glycol having an average molecular weight of 150 to 2000 wherein the branched saturated fatty acid moiety has from 11 to 21 carbon atoms (hereinafter referred to as "component (IV)").

When the above composition is used as an emulsifying or solubilizing agent, vegetable oils and highly polar oils synthesized as emollient oils, which have heretofore been considered difficult to emulsify, can easily be emulsified or solubilized, and ideal emulsions having a good color with a reduced odor can be obtained.

As the vegetable oil to be emulsified or solubilized, there can be mentioned liquid vegetable oils composed of triglycerides rich in unsaturated alkyl groups, such as camellia oil, olive oil, safflower oil, rapeseed oil, palm oil and cotton seed oil, and as the synthetic ester oil, there can be mentioned esters having at least one branched alkyl group, which are derived from branched or linear higher fatty acids and branched or linear higher alcohols, such as 2-heptylundecyl isostearate, glycerol tri-2-ethylhexanoate, hexadecyl 2-ethylhexanoate, hexadecyl isostearate and hexadecyl isotridecanoate. These vegetable oils and synthetic ester oils are widely used in cosmetics. By using the composition of the present invention, it is possible for the first time to employ these oils, in the emulsified or solubilized state, in cosmetics. Namely, it is possible to incorporate these vegetable oils or synthetic ester oils into various cosmetic creams such as sun creams and hair creams and other cosmetics such as lotions. By incorporation of these oils, emulsified or solubilized by the composition of the present invention, it is possible to obtain milder cosmetics having a higher emollient effect than conventional cosmetics composed mainly of mineral oils. Of course, the composition of the present invention also has an excellent emulsifying power for mineral oils and animal oils, that can also be emulsified by conventional emulsifiers, as well as the above-mentioned vegetable oils and synthetic ester oils.

The polyoxyethylene sorbitol branched saturated fatty acid ester (I) that is used in the present invention is, as is seen from the formula (A), an ester formed by esterifying an ethylene oxide adduct of sorbitol with a branched saturated fatty acid having 11 to 21 carbon atoms, such as isostearic acid or isotridecanoic acid. It is necessary that among the total of the 6 hydroxyl groups of sorbitol, from 3 to 6 of them, on the average, of the mixture should be esterified. More specifically, in the general formula (A), 3 to 6 of the 6 X's are acyl groups, the rest being hydrogen. (In the description given hereinafter, the number of such acyl groups will be called "the degree of esterification"). If the degree of esterification is lower than in the above range i.e. from 3 to 6, the emulsifying property is diminished and a good and stable emulsion cannot be obtained.

As the fatty acid employed for the above esterification, there are preferably employed branched saturated fatty acids having 11 to 21 carbon atoms, such as isostearic acid, isotridecanoic acid and isoundecanoic acid. When a linear saturated fatty acid such as stearic acid or palmitic acid is used instead of the specified branched acids, the emulsifying property is diminished, and the resulting ester is solid at room temperature and hence, good results cannot be obtained. When a linear unsaturated fatty acid such as oleic acid or linoleic acid is used, a sufficient emulsifying or solubilizing property can be attained, but the resulting ester is inferior to an ester derived from a liquid branched saturated fatty acid, according to the invention, with respect to its chemical stability (the resistance to changes with the passage of time), smell, color and resistance to discoloration.

The above ester is prepared by conventional procedures by adding sorbitol to a solvent such as xylene, adding ethylene oxide to sorbitol in the presence of a basic catalyst to effect the addition reaction, adding a branched saturated fatty acid in an amount of 3 to 6 moles per mole of the ethylene oxide adduct of sorbitol, heating the mixture at 180° to 240° C. to effect the esterification reaction, and then decolorizing and purifying the resulting ester.

It is necessary that the composition of the present invention comprises 58 to 95% by weight of the component (I), 0.2 to 2.5% by weight of the component (II), 2.5 to 6.0% by weight of the component (III) and 2 to 35% by weight of the component (IV). If this requirement is not satisfied, the emulsifying property to vegetable oils and synthetic ester oils is diminished and the resulting emulsion is so poor in the stability that when it is allowed to stand, the emulsion is destroyed in a short time and phase separation takes place.

In view of the properties of the oils which are to be emulsified or solubilized by the emulsifying or solubilizing composition of the present invention, the composition of the invention is utilized most effectively in the field of cosmetics. Of course, the composition of the present invention can also be used as an emulsifying or solubilizing agent in any fields where the foregoing oils are used, for example, in the fields of foods, fiber oiling agents, detergents, metal processing oils and the like.

The features of the present invention will now be described in greater detail by reference to the following illustrative Examples: In the Examples all references to "%" are by weight unless otherwise indicated.

EXAMPLE 1

Emulsifying agent compositions containing the ingredients indicated below were prepared and emulsifying tests were made on various oils by using these compositions.

| Ingredients | Composition (%) | |
| --- | --- | --- |
|  | Emulsifier (a) | Emulsifier (b) |
| Component (I)* | 70 | 70 |
| Component (II) (sodium) isostearate) | 1.2 | 1.2 |
| Component (III) (isostearic acid) | 5.0 | 5.0 |
| Component (IV) (polyethylene glycol isostearate having an average molecular weight of 600) | 23.8 | 23.8 |

*: In the component (I) of the emulsifier (a) the average total mole number of added ethylene oxide units was 30, and in the component (I) of the emulsifier (b) the total mole number of added ethylene oxide units was 60. Esterification was performed with isostearic acid. In each of the emulsifiers (a) and (b), 7 samples differing in the degree of esterification from 0 to 6 were tested.

TEST METHOD

A mixture of 20 parts (by weight; the same shall apply hereinafter) of an oil component, 5 parts of the emulsifying composition and 75 parts of deionized water were emulsified at a temperature of 70° C., using an agitation vane rotating at 600 rpm, according to the phase inversion emulsification method. The emulsifiability and stability of the resulting emulsion were evaluated according to the following standards:

(1) Emulsifiability:

The state of the as-emulsified emulsion was observed with the naked eye and by a microscope and the emulsifiability was evaluated according to the following standards:

A: bluish white emulsion of fine particles having an average particle size smaller than $1\mu$ as measured under a microscope B: milky white emulsion of particles having an average particle size of 1 to $5\mu$ as measured under a microscope C: opaque emulsion of crude particles having an average particle size larger than $5\mu$ as measured under a microscope (2) Stability:

The emulsion formed was allowed to stand still at 25° C. for 7 days, and the state of the emulsion was examined. The stability was evaluated according to the following standards:

(−): homogeneous, no phase separation found (+): slight formation of an oil phase by coalescence or an aqueous phase by separation of water was observed (++): oil phase formed by coalescence or aqueous phase formed by separation of water was clearly observed (+++): both oil phase formed by coalescence and aqueous phase formed by separation of water were clearly observed The test results are shown in Table 1.

Table 1

| Emulsifying Agent Composition | Oil Emulsified | | Degree of Estrification of Component (I) (number of acyl groups in formula (A)) | | | | | | |
|---|---|---|---|---|---|---|---|---|---|
| | | | 0 | 1 | 2 | 3 | 4 | 5 | 6 |
| (a) | olive oil | emulsifiability | C | B | B | A | A | A | B |
| | | stability | (+++) | (+++) | (+++) | (+) | (−) | (−) | (++) |
| | glycerol tri-2-ethylhexanoate | emulsifiability | C | C | B | A | A | A | B |
| | | stability | (+++) | (+++) | (+++) | (−) | (−) | (+) | (++) |
| | hexadecyl-2-ethylhexanoate | emulsifiability | C | C | C | B | A | A | A |
| | | stability | (+++) | (+++) | (+++) | (+) | (−) | (−) | (−) |
| (b) | olive oil | emulsifiability | C | C | B | A | A | A | B |
| | | stability | (+++) | (+++) | (+++) | (++) | (−) | (−) | (−) |
| | glycerol tri-2-ethylhexanoate | emulsifiability | C | B | A | A | A | A | A |
| | | stability | (+++) | (+++) | (++) | (−) | (−) | (−) | (−) |
| | hexadecyl-2-ethylhexanoate | emulsifiability | C | C | C | B | A | A | |
| | | stability | A (+++) | (+++) | (+++) | (++) | (−) | (−) | (−) |

From the results shown in Table 1, it will be understood that the compositions of the present invention, in which the average degree of esterification (the number of acyl groups as X in the general formula (A)) in the component (I) is in the range of from 3 to 6, have an excellent emulsifying property and form emulsions, having good stability, whereas when a component (I) having a degree of esterification not higher than 2 is employed, the emulsifying property is bad, and the stability of the resulting emulsion is low and phase separation takes place.

EXAMPLE 2 (Emulsification Of Olive Oil)

An emulsifying test for olive oil was carried out using various emulsifying compositions as listed in Table 2. In each run, an emulsion was prepared from 20 parts of olive oil, 5 parts of the emulsifier composition and 75 parts of deionized water. The test and evaluation methods were the same as described in Example 1. The results obtained are shown in Table 2.

Table 2

| | Type of Emulsifier Component I | $n_1 + n_2 + n_3 + n_4 + n_5 + n_6$ | Emulsifier Composition Ratio (% by weight) | | | |
|---|---|---|---|---|---|---|
| Product[1] of Present Invention | POE sorbitol branched fatty acid ester type | | (I) | (II) | (III) | (IV) |
| | | 10 | 73.5 | 1.0 | 4.8 | 20.7 |
| | | 30 | 85.0 | 1.2 | 5.0 | 8.8 |
| | | 40 | 90.0 | 0.8 | 4.4 | 4.8 |
| | | 60 | 70.0 | 1.2 | 5.0 | 23.8 |
| Comparative Product (1)[2] | " | 30 | 70.0 | 0 | 4.5 | 25.5 |
| | | 30 | 69.8 | 0.3 | 0 | 29.9 |
| | | 30 | 40.2 | 0.7 | 4.2 | 54.9 |
| | | 60 | 70.0 | 0 | 3.8 | 26.2 |
| Comparative Product (2)[3] | POE sorbitol linear unsaturated fatty acid ester type | 30 | 64.5 | 1.0 | 3.5 | 31.0 |
| | | 40 | 63.0 | 1.0 | 3.5 | 32.5 |
| Comparative Product (3) | POE sorbitan ester/sorbitan ester type | POE sorbitan mono-oleate/sorbitan mono-oleate** POE sorbitan trioleate | | | | |
| Comparative Product (4) | POE fatty acid ester/glycerin ester type | POE (8) stearate/glycerol monostearate POE (50) stearate/glycerol monostearate | | | | |
| Comparative Product (5) | POE alkyl ether type | POE (5) oleyl ether POE (7) cetyl ether POE (9) oleyl ether | | | | |
| Comparative Product (6) | polymer type | polyoxyethylene-polyoxypropylene condensate | | | | |
| Comparative Product (7) | soap type | sodium oleate potassium oleate | | | | |

| | HLB $(20(1 - \frac{S}{A}))$ | Emulsion type (o/w or w/o) | Emulsifiability (just after preparation) | Stability (after standing at 25° C for 7 days) |
|---|---|---|---|---|
| Product[1][1] of Present Invention | 7.8 | o/w | A | (−) |
| | 10.1 | o/w | A | (−) |
| | 11.7 | o/w | A | (−) |
| | 12.0 | o/w | AB | (+++) |
| Comparative Product(1)[2] | 10.3 | o/w | C | (+++) |
| | 10.3 | o/w | C | (++) |
| | 10.1 | o/w | B | (++) |
| | 13.8 | o/w | C | (+++) |
| Comparative Product(2)[3] | 10.4 | o/w | A | (−) |
| | 11.8 | o/w | A | (−) |
| Comparative Product(3) | 8.0 | o/w | C | (+++) |
| | 10.0 | o/w | C | (+++) |
| | 12.0 | o/w | C | (+++) |
| | 11.0 | o/w | B | (+) |
| Comparative | 8.0 | o/w | C | (−)* |

Table 2-continued

| | | | | |
|---|---|---|---|---|
| Product(4) | 10.0 | o/w | C | (−)* |
| | 12.0 | o/w | C | (−)* |
| Comparative Product(5) | 8.8 | o/w | C | (+++) |
| | 10.7 | o/w | C | (+++) |
| | 12.1 | o/w | C | (+++) |
| Comparative Product(6) | — | o/w | C | (+++) |
| Comparative Product(7) | — | o/w | B | (+++) |
| | — | o/w | B | (+++) |

*Since the viscosity of the emulsion was extremely high, phase separation was not caused in spite of low emulsifiability.
** POE(n): n denotes the mole number of added ethylene oxide units.

Note[1] The constituents of the product of the present invention were as follows:

| $n_1+n_2+n_3+n_4+n_5+n_6$ | Component (I) | Average Degree of Esterification of (I) | Component (II) | Component (IV) | of PEG of (IV) | Average Molecular Weight |
|---|---|---|---|---|---|---|
| 10 | POE sorbitol isotridecanoate | 3.0 | sodium iso-tridecanoate | isotridecanoic acid | polyethylene glycol isotridecanoate | 150 |
| 30 | POE sorbitol isostearate | 4.0 | sodium isostearate | isostearic acid | polyethylene glycol isostearate | 450 |
| 40 | " | 4.5 | " | " | " | 600 |
| 60 | " | 5.5 | sodium stearate | " | " | 900 |
| 80 | " | 6.0 | sodium isostearate | " | " | 1200 |
| 100 | " | 6.0 | " | " | " | 1600 |

Note[2] The constituents of the comparative product (1) were as follows:

| $n_1+n_2+n_3+n_4+n_5+n_6$ | Component (I) | Average Degree of Esterification of (I) | Component (II) | Component (III) | Component (IV) | Average Molecular Weight of PEG of (IV) |
|---|---|---|---|---|---|---|
| 30 | POE sorbitol isostearate | 3.0 | sodium isostearate | isostearic acid | polyethylene glycol isostearate | 450 |
| 30 | " | 4.0 | " | " | " | 450 |
| 30 | " | 4.0 | " | " | " | 450 |
| 60 | " | 5.5 | " | " | " | 900 |

Note[3] The constituents of the comparative product (2) were as follows:

| $n_1+n_2+n_3+n_4+n_5+n_6$ | Component (I) | Average Degree of Esterification of (I) | Component (II) | Component (III) | Component (IV) | Average Molecular Weight of PEG of (IV) |
|---|---|---|---|---|---|---|
| 30 | POE sorbitol oleate | 4.5 | sodium oleate | oleic acid | polyethylene glycol oleate | 450 |
| 40 | " | 4.5 | " | " | " | 600 |

The constituents of the product[1] of the present invention, comparative product (1)[2] and comparative product (2)[3] in the following Tables 3 and 4 are the same as set forth above.

EXAMPLE 3 (Emulsification of 2-Heptylundecyl Isostearate)

A mixture of 20 parts of a synthetic ester oil obtained by esterification of 2-heptylundecanol with isostearic acid, 5 parts of an emulsifier composition and 75 parts of deionized water was emulsified and tested in the same manner as described in Example 2. The results obtained are shown in Table 3.

Table 3
(Emulsification of 2-Heptylundecyl Isostearate)

| Product[1] of Present Invention | Type of Emulsifier Component I | $n_1 + n_2 + n_3 + n_4 + n_5 + n_6$ | Emulsifier Composition Ratio (% by weight) | | | |
|---|---|---|---|---|---|---|
| | | | (I) | (II) | (III) | (IV) |
| | POE sorbitol branched fatty acid ester type | 10 | 73.5 | 1.0 | 4.8 | 20.7 |
| | | 30 | 85.0 | 1.2 | 5.0 | 8.8 |
| | | 40 | 90.0 | 0.8 | 4.4 | 4.8 |
| | | 60 | 70.0 | 1.2 | 5.0 | 23.8 |
| | | 80 | 64.5 | 1.5 | 4.5 | 29.5 |
| | | 100 | 63.0 | 1.0 | 4.5 | 31.5 |
| Comparative Product (1)[2] | " | 30 | 70.0 | 0 | 4.5 | 25.5 |
| | | 30 | 69.8 | 0.3 | 0 | 29.9 |
| | | 30 | 40.2 | 0.7 | 4.2 | 54.9 |
| | | 60 | 70.0 | 0 | 3.8 | 26.2 |
| Comparative Product (2)[3] | POE sorbitol linear unsaturated fatty acid ester type | 30 | 64.5 | 1.0 | 3.5 | 31.0 |
| | | 40 | 63.0 | 1.0 | 3.5 | 32.5 |
| Comparative Product (3) | POE sorbitan ester/ sorbitan ester type | POE (20) sorbitan mono-oleate/sorbitan mono-oleate** POE (20) sorbitan trioleate | | | | |
| Comparative Product (4) | POE fatty acid ester/ glycerin ester type | POE (8) stearate/glycerol monostearate POE (50) stearate/glycerol monostearate | | | | |
| Comparative Product (5) | POE alkyl ether type | POE (5) oleyl ether POE (7) cetyl ether POE (9) oleyl ether | | | | |
| Comparative Product (6) | polymer type | polyoxyethylene-polyoxypropylene condensate | | | | |
| Comparative Product (7) | soap type | sodium oleate potassium oleate | | | | |

Table 3-continued
(Emulsification of 2-Heptylundecyl Isostearate)

| Product[1] of Present Invention | HLB $(20(1 - \frac{S}{A}))$ | Emulsion Type (o/w or w/o) | Emulsifiability (just after preparation) | Stability (after standing at 25° C for 7 days) |
|---|---|---|---|---|
| | 7.8 | o/w | B | (+) |
| | 10.1 | o/w | A | (−) |
| | 11.7 | o/w | A | (−) |
| | 12.0 | o/w | A | (−) |
| | 13.3 | o/w | A | (−) |
| | 14.3 | o/w | B | (−) |
| Comparative Product (1)[2] | 10.3 | o/w | C | (+++) |
| | 10.3 | o/w | C | (+++) |
| | 10.1 | o/w | B | (+++) |
| | 13.8 | o/w | C | (+++) |
| Comparative Product (2)[3] | 10.4 | o/w | A | (−) |
| | 11.8 | o/w | A | (−) |
| Comparative Product (3) | 8.0 | o/w | C | (+++) |
| | 10.0 | o/w | A | (++) |
| | 12.0 | o/w | C | (+++) |
| | 11.0 | o/w | B | (+++) |
| Comparative Product (4) | 8.0 | o/w | C | (−)* |
| | 10.0 | o/w | C | (−)* |
| | 12.0 | o/w | C | (++) |
| Comparative Product (5) | 8.8 | o/w | C | (+++) |
| | 10.7 | o/w | C | (+++) |
| | 12.1 | o/w | C | (+++) |
| Comparative Product (6) | — | o/w | C | (+++) |
| Comparative Product (7) | — | o/w | C | (+++) |
| | — | o/w | C | (+++) |

*Since the viscosity of the emulsion was extremely high, no phase separation was observed in spite of low emulsifiability.
**POE(n): n indicates the mole number of added ethylene oxide.

EXAMPLE 4 (Emulsification of Glycerol Tri-2-ethylhexanoate)

A mixture of 20 parts of a synthetic ester oil (glycerol tri-2-ethylhexanoate), 5 parts of an emulsifier composition and 75 parts of deionized water were emulsified and tested in the same manner as described in Example 2. The results obtained are shown in Table 4.

Table 2
(Emulsification of Glycerol Tri-2-ethylhexanoate)

| Product[1] Invention | Type of Emulsifier Component I | $n_1 + n_2 + n_3 + n_4 + n_5 + n_6$ | Emulsifier Composition Ratio (% by weight) | | | |
|---|---|---|---|---|---|---|
| | | | (I) | (II) | (III) | (IV) |
| | POE sorbitol branched fatty acid ester type | 10 | 7.35 | 1.0 | 4.8 | 2.7 |
| | | 30 | 85.0 | 1.2 | 5.0 | 8.8 |
| | | 40 | 90.0 | 0.8 | 4.4 | 4.8 |
| | | 60 | 70.0 | 1.2 | 5.0 | 23.8 |
| | | 80 | 64.5 | 1.5 | 4.5 | 2.5 |
| | | 100 | 63.0 | 1.0 | 4.5 | 31.5 |
| Comparative Product (1)[2] | " | 30 | 70.0 | 0 | 4.5 | 25.5 |
| | | 30 | 69.8 | 0.3 | 0 | 2.9 |
| | | 30 | 40.2 | 0.7 | 4.2 | 54.9 |
| | | 60 | 70.0 | 0 | 3.8 | 26.2 |
| | | 30 | 64.5 | 1.0 | 3.5 | 31.0 |
| Comparative Product (2)[3] | POE sorbitol linear unsaturated fatty acid ester type | 40 | 63.0 | 1.0 | 3.5 | 32.5 |
| Comparative Product (3) | POE sorbitan ester/ sorbitan ester type | POE(20) sorbitan mono-oleate/sorbitan mono-oleate** | | | | |
| | | POE(20) sorbitan trioleate | | | | |
| Comparative Product (4) | POE fatty acid ester/ glycerin ester type | POE(8) stearate/glycerol monostearate | | | | |
| | | POE(50) stearate/glycerol monostearate | | | | |
| Comparative Product (5) | POE alkyl ether type | POE(5) oleyl ether | | | | |
| | | POE(7) cetyl ether | | | | |
| | | POE(9) oleyl ether | | | | |
| Comparative Product (6) | polymer type | polyoxyethylene-polyoxypropylene condensate | | | | |
| Comparative Product (7) | soap type | sodium oleate | | | | |
| | | potassium oleate | | | | |

| Product[1] of Present Invention | HLB $(20(1 - \frac{S}{A}))$ | Emulsion Type (o/w or w/o) | Emulsifiability (just after preparation) | Stability (after standing at 25° C for 7 days) |
|---|---|---|---|---|
| | 7.8 | o/w | A | (−) |
| | 10.1 | o/w | A | (−) |
| | 11.7 | o/w | A | (−) |
| | 12.0 | o/w | A | (−) |
| | 13.3 | o/w | A | (−) |
| | 14.3 | o/w | A | (−) |
| Comparative Product (1)[2] | 10.3 | o/w | C | (+++) |
| | 10.3 | o/w | B | (+++) |
| | 10.1 | o/w | A | (+) |
| | 13.8 | o/w | C | (+++) |
| Comparative Product (2)[3] | 10.4 | o/w | A | (−) |
| | 11.8 | o/w | A | (−) |

Table 2-continued

| | | (Emulsification of Glycerol Tri-2-ethylhexanoate) | | | |
|---|---|---|---|---|---|
| Comparative Product (3) | 8.0 | o/w | A | | (+) |
| | 10.0 | o/w | C | | (++) |
| | 12.0 | o/w | C | | (+++) |
| | 11.0 | o/w | B | | (+++) |
| Comparative Product (4) | 8.0 | o/w | C | | (−)* |
| | 10.0 | o/w | C | | (−)* |
| | 12.0 | o/w | C | | (+++) |
| Comparative Product (5) | 8.8 | o/w | C | | (+++) |
| | 10.7 | o/w | C | | (+++) |
| | 12.1 | o/w | C | | (+++) |
| Comparative Product (6) | — | o/w | C | | (+++) |
| Comparative Product (7) | — | o/w | B | | (+++) |
| | — | o/w | C | | (+++) |

*Since the viscosity of the emulsion was extremely high, no phase separation was observed in spite of low emulsifiability.
**POE(n): n indicates the mole number of added ethylene oxide.

As will be apparent from the results shown in Tables 2 to 4, when known emulsifiers are used, vegetable oils or synthetic ester oils cannot be emulsified at all or they can be emulsified only insufficiently. In contrast, when the emulsifying composition of the present invention is used, such oils can easily be emulsified and good emulsions of excellent stability can be obtained. Even when the same components as used in the present invention are employed, if the weight ratio of the components is outside the ranges specified in the present invention, both the emulsifiability and the stability of the emulsions are diminished.

EXAMPLE 5 (Resistance to Photo-Discoloration)

The emulsifier agent compositions set forth in Table 5 were subjected to a photo-discoloration test. Each sample was exposed to artificial sunlight for 24 hours by using a sun-shine weather-meter, and the hue of each sample according to the Gardner color scale was measured before and after the exposure. The results are shown in Table 5.

As will be apparent from the results shown in Table 5, the polyoxyethylene sorbitol branched saturated fatty acid ester which is the main component (I) of the emulsifying composition of the present invention is superior to that of the polyoxyethylene sorbitol linear unsaturated fatty acid ester with respect to the resistance or stability to photo-discoloration.

EXAMPLE 6 (Sensory Odor Test)

A product (A) of the present invention and a comparative product (B), each having a composition as described below, were subjected to the sensory odor test by a panel of 30 persons according to the pair-comparison method of Scheffe. The results obtained are shown in Table 6.

| Composition (A) (present invention): | |
|---|---|
| (I) Polyoxyethylene (p = 30) sorbitol isostearate (average esterification degree = 4.5) | 64.5% |
| (II) Sodium isostearate | 1.2% |
| (III) Isostearic acid | 3.5% |
| (IV) Polyethylene glycol isostearate (average molecular weight of PEG being 450) | 30.8% |

| Composition (B) (comparison): | |
|---|---|
| (I) Polyoxyethylene (p = 30) sorbitol oleate (average esterification degree = 4.5) | 60.5% |
| (II) Sodium oleate | 1.0% |

Table 5

| | Type of Emulsifier | $n_2+n_3+n_4+n_5+n_6$ | $n_1+$ Composition (% by weight) | | | | Hue (Gardner Color Scale) | |
|---|---|---|---|---|---|---|---|---|
| | | | (I) | (II) | (III) | (IV) | before exposure | after exposure |
| Product[1] of Present Invention | POE sorbitol isostearate type | 30 | 64.5 | 1.2 | 3.5 | 30.8 | 2 | 2 |
| | | 40 | 63.0 | 1.2 | 3.5 | 30.8 | 3 | 3-4 |
| | | 60 | 61.5 | 1.2 | 3.5 | 30.8 | 2 | 2 |
| Comparative Product[2] | POE sorbitol oleate type | 30 | 64.5 | 1.0 | 3.5 | 31.0 | 2 | 4 |
| | | 40 | 63.0 | 1.0 | 3.5 | 31.0 | 4 | 5-6 |
| | | 60 | 61.5 | 1.0 | 3.5 | 31.0 | 3 | 4-5 |

[1] The constituents of the product of the present invention were as follows:

| $n_1+n_2+n_3+n_4+n_5+n_6$ | Component (I) | Average Degree of Esterification of (I) | Component (II) | Component (III) | Component (IV) | Average Molecular Weight of PEG of (IV) |
|---|---|---|---|---|---|---|
| 30 | POE sorbitol isostearate | 4.5 | sodium isostearate | isostearic acid | polyethylene glycol isostearate | 450 |
| 40 | ditto | 4.5 | ditto | ditto | ditto | 600 |
| 60 | ditto | 4.5 | ditto | ditto | ditto | 900 |

[2] The constituents of the comparative product were as follows:

| $n_1+n_2+n_3+n_4+n_5+n_6$ | Component (I) | Average Degree of Esterification of (I) | Component (II) | Component (III) | Component (IV) | Average Molecular Weight of PEG of (IV) |
|---|---|---|---|---|---|---|
| 30 | POE sorbitol oleate | 4.5 | sodium oleate | oleic acid | polyethylene glycol oleate | 450 |
| 40 | ditto | 4.5 | ditto | ditto | ditto | 600 |
| 60 | ditto | 4.5 | ditto | ditto | ditto | 900 |

-continued

| | | |
|---|---|---|
| (III) | Oleic acid | 4.3% |
| (IV) | Polyethylene glycol oleate (average molecular weight of PEG being 458) | 34.2% |

Table 6

| Order | B is better than A (−2) | B is slightly better than A(−1) | no substantial difference (0) | A is slightly better than B(1) | A is better than B(2) |
|---|---|---|---|---|---|
| A → B | 1 | 1 | 4 | 3 | 6 |
| B → A | 0 | 3 | 2 | 7 | 3 |
| Total | 1 | 4 | 6 | 10 | 9 |

When the above data were subjected to $t$ inspection, the result of $t(\alpha) = 3.514 > t(n-1.0.01) = 2.756$ ($n = 30$) was obtained. Thus, it was found that the odor of A was more pleasant than the odor of B with a significance level of 1%.

Thus, it is apparent that with respect to the odor, a branched saturated fatty acid moiety is superior to a linear unsaturated fatty acid moiety for the fatty acid moiety of the polyoxyethylene sorbitol fatty acid which is the main component (I) of the composition of the present invention.

EXAMPLE 7 (o/w Type Cream)

An emulsifying composition comprising the following ingredients was prepared:

| | |
|---|---|
| (I) Polyoxyethylene (p = 10) sorbitol isotridecanoate (average esterification degree = 3.0) | 73.5% |
| (II) Potassium isotridecanoate | 1.0% |
| (III) Isotridecanoate acid | 4.8% |
| (IV) Polyethylene glycol isotridecanoate (average molecular weight of PEG equals 150) | 20.7% |

The composition was a yellowish brown liquid having a specific gravity ($d_4^{20}$) of 0.981, a viscosity of 256 cps as measured at 20° C., a saponification value of 116.8 and an HLB value of 7.2.

An o/w type cream having the following composition was prepared by using the thus prepared emulsifying composition:

| | | |
|---|---|---|
| (1) | Olive oil | 25 parts |
| | Bees wax | 3 parts |
| | Hydrous lanolin | 7 parts |
| | Paraffin wax | 5 parts |
| | Emulsifying composition | 6 parts |
| (2) | Sorbitol | 15 parts |
| | Water | 39 parts |
| (3) | Perfume, antiseptic, etc. | minor amounts |

The ingredients of group (1) and of (2) were heated and melted at 80° C. separately, and the melts were mixed vigorously to effect emulsification. While the resulting emulsion was being cooled, the ingredients of group (3) were added thereto and dispersed therein. The resulting cream had a very good emulsion state.

EXAMPLE 8 (Milky Lotion)

| | | |
|---|---|---|
| (I) | Polyoxyethylene (p = 30) sorbitol isostearate (average esterification degree = 4.5) | 64.5% |
| (II) | Sodium isostearate | 1.2% |
| (III) | Isostearic acid | 3.5% |
| (IV) | Polyethylene glycol isostearate (average molecular weight of PEG being 450) | 30.8% |

The thus prepared emulsifying composition was a yellowish brown liquid having a specific gravity ($d_4^{20}$) of 1.012, a viscosity of 390 cps as measured at 20° C., a saponification value of 94.2 and an HLB value of 10.4.

In the same manner as described in Example 7, a milky lotion comprising the following ingredients was prepared by using the thus obtained emulsifying composition:

| | | |
|---|---|---|
| (1) | Olive oil | 10 parts |
| | Hexadecyl 2-ethylhexanoate | 5 parts |
| | Cetyl alcohol | 2 parts |
| | Bees wax | 2 parts |
| | Emulsifying composition | 5 parts |
| (2) | Sorbitol | 15 parts |
| | Water | 61 parts |
| (3) | Perfume, antiseptic, etc. | appropriate amounts |

The resulting milky lotion had a very good emulsion state, and the emulsion system was stable even after it had been allowed to stand for a long time.

The embodiments of the invention in which an exclusive property or privelege is claimed are defined as follows:

1. An emulsifying or solubilizing composition, consisting essentially of

I. from 58 to 95 percent by weight of a surface active agent having the formula

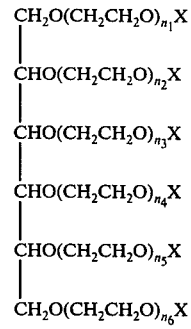

wherein the sum of $n_1$ to $n_6$ is from 10 to 100 and, on the average, from 3 to 6 of the X's are branched saturated acyl groups having from 11 to 21 carbon atoms and the balance of the X's are hydrogen, II. from 0.5 to 2.5 percent by weight of an alkali metal salt of a linear or branched fatty acid having from 11 to 21 carbon atoms, III. from 2.5 to 6.0 percent by weight of a linear or branched fatty acid having 11 to 23 carbon atoms, and IV. from 2 to 35 percent by weight of a branched saturated fatty acid ester of polyethylene glycol having an average molecular weight of 150 to 2000, wherein the branched saturated fatty acid ester moiety has from 11 to 21 carbon atoms.

2. A composition as claimed in claim 1 in which said acyl group is isostearyl, component II is sodium isostearate or sodium stearate, component III is isostearic acid and component IV is polyethylene glycol isostearate.

3. A composition as claimed in claim 1 in which said acyl group is isotridecanoyl, component II is sodium isotridecanoate, component III is isotridecanoic acid and component IV is polyethylene glycol isotridecanoate.

4. A composition as set forth in claim 1 wherein the sum of $n_1$ to $n_6$ is from 28 to 30, and from 3.5 to 4.5 of the X's on the average of the mixture are branched saturated acyl groups having 11 to 21 carbon atoms, the balance being hydrogens.

5. A composition as set forth in claim 1 wherein the sum of $n_1$ to $n_6$ is from 38 to 52, and from 4.2 to 5.3 of the X's on the average of the mixture are branched saturated acyl groups having 11 to 21 carbon atoms, the balance being hydrogens.

6. A composition as set forth in claim 1 wherein the sum of $n_1$ to $n_6$ is from 55 to 65, and from 4.4 to 5.5 of the X's on the average of the mixture are branched saturated acyl groups having 11 to 21 carbon atoms, the balance being hydrogens.

7. An oil-in-water emulsion containing as an emulsifier for the oil phase, an effective emulsifying amount of a composition as claimed in claim 1.

8. An emulsion as claimed in claim 7, in which said oil component consists of a liquid vegetable oil consisting essentially of triglycerides containing several unsaturated aliphatic hydrocarbon groups or synthetic ester oils having at least one branched alkyl group obtained by reacting a branched or linear higher fatty acid with a branched or linear higher alcohol.

9. An emulsion as claimed in claim 7 in which the oil component is selected from the group consisting of camellia oil, olive oil, safflower oil, rapeseed oil, palm oil and cotton seed oil.

10. An emulsion as claimed in claim 7 in which the oil component is selected from the group consisting of 2-heptylundecyl isostearate, glycerol-tris-2-ethylhexanoate, hexadecyl-2-ethyl-hexanoate, hexadecyl isostearate and hexadecyl isotridecanoate.

* * * * *